(12) United States Patent
Sislian et al.

(10) Patent No.: US 9,988,691 B2
(45) Date of Patent: Jun. 5, 2018

(54) SYSTEM FOR AIRBORNE BACTERIAL SAMPLE COLLECTION AND ANALYSIS

(75) Inventors: Patrick Sislian, Toluca Lake, CA (US); Ramzi Nasr, Falls Church, VA (US); Mazen Nasr, Cerritos, CA (US)

(73) Assignee: Deton Corp., Pasadena, CA (US)

(*) Notice: Subject to any disclaimer, the term of this patent is extended or adjusted under 35 U.S.C. 154(b) by 1003 days.

(21) Appl. No.: 13/807,193

(22) PCT Filed: Jul. 1, 2011

(86) PCT No.: PCT/US2011/042854
§ 371 (c)(1),
(2), (4) Date: Apr. 30, 2013

(87) PCT Pub. No.: WO2012/006250
PCT Pub. Date: Jan. 12, 2012

(65) Prior Publication Data
US 2013/0217029 A1 Aug. 22, 2013

Related U.S. Application Data

(60) Provisional application No. 61/361,804, filed on Jul. 6, 2010.

(51) Int. Cl.
*A61B 5/08* (2006.01)
*G01N 1/00* (2006.01)
(Continued)

(52) U.S. Cl.
CPC .............. *C12Q 1/689* (2013.01); *A61B 5/082* (2013.01); *A61B 5/097* (2013.01); *G01N 1/2208* (2013.01);
(Continued)

(58) Field of Classification Search
None
See application file for complete search history.

(56) References Cited

U.S. PATENT DOCUMENTS 3,760,831 A * 9/1973 Colvin ................... G05D 7/03
137/115.09
3,858,573 A 1/1975 Ryan
(Continued)

FOREIGN PATENT DOCUMENTS

CN 1676173 A 10/2005
CN 101379388 A 3/2009
(Continued)

OTHER PUBLICATIONS

Sislian et al., "Bacterial aerosol neutralization by aerodynamic shocks using a novel impactor system: Design and computation", Chemical Engineering Science, Feb. 28, 2009, vol. 64, pp. 1953-1967.
(Continued)

*Primary Examiner* — Etsub Berhanu
(74) *Attorney, Agent, or Firm* — KPPB LLP

(57) ABSTRACT

An aerosol biological collector/analyzer, and method of collecting and analyzing an aerosol sample for diagnosis is provided. In particular, the current invention is directed to an airborne aerosol collection and bacterial analysis system and method, capable of collecting an airborne aerosol sample and preparing it for analysis via aerodynamic shock in a single-step.

21 Claims, 11 Drawing Sheets

(51) Int. Cl.
*G01N 1/22* (2006.01)
*C12Q 1/68* (2018.01)
*A61B 5/097* (2006.01)
*G01N 33/497* (2006.01)

(52) U.S. Cl.
CPC ... *G01N 33/497* (2013.01); *G01N 2001/2217* (2013.01); *G01N 2001/2244* (2013.01)

(56) References Cited

U.S. PATENT DOCUMENTS

| | | |
|---|---|---|
| 3,880,591 A | 4/1975 | Burroughs et al. |
| 4,133,202 A * | 1/1979 | Marple .............. G01N 15/0255 73/28.04 |
| 4,297,871 A | 11/1981 | Wright et al. |
| 4,558,708 A | 12/1985 | Labuda et al. |
| 4,572,208 A * | 2/1986 | Cutler .................... A61B 5/083 128/205.12 |
| 4,640,140 A | 2/1987 | Burghoffer et al. |
| 4,678,488 A | 7/1987 | Howard et al. |
| 5,042,501 A | 8/1991 | Kenny et al. |
| 5,046,491 A | 9/1991 | Derrick |
| 5,081,871 A | 1/1992 | Glaser |
| 5,211,181 A | 5/1993 | Delente |
| 5,253,641 A | 10/1993 | Choate |
| 5,372,126 A | 12/1994 | Blau |
| 5,409,014 A * | 4/1995 | Napoli ................... A61B 5/208 600/575 |
| 5,465,728 A | 11/1995 | Phillips et al. |
| 5,533,513 A | 7/1996 | Ueda et al. |
| 5,573,005 A | 11/1996 | Ueda et al. |
| 5,739,412 A | 4/1998 | Stock et al. |
| 5,787,885 A | 8/1998 | Lemelson |
| 5,826,577 A | 10/1998 | Perroz et al. |
| 5,855,652 A | 1/1999 | Talley |
| 5,902,385 A | 5/1999 | Willeke et al. |
| 5,904,752 A | 5/1999 | Willeke |
| 6,053,874 A | 4/2000 | Kharitonov et al. |
| 6,217,636 B1 | 4/2001 | McFarland |
| 6,468,330 B1 | 10/2002 | Irving et al. |
| 6,520,034 B1 | 2/2003 | Masquelier et al. |
| 6,582,376 B2 | 6/2003 | Baghdassarian |
| 6,585,661 B1 | 7/2003 | Hunt et al. |
| 6,723,056 B1 | 4/2004 | Alving et al. |
| 6,726,637 B2 | 4/2004 | Phillips |
| 6,729,196 B2 | 5/2004 | Moler et al. |
| 6,854,344 B2 | 2/2005 | Cornish et al. |
| 7,073,402 B2 | 7/2006 | Trakumas et al. |
| 7,118,537 B2 | 10/2006 | Baddour |
| 7,153,272 B2 | 12/2006 | Talton |
| 7,282,032 B2 | 10/2007 | Miller |
| 7,297,120 B2 | 11/2007 | Tsukashima et al. |
| 7,364,553 B2 | 4/2008 | Paz et al. |
| 7,377,901 B2 | 5/2008 | Djupesland et al. |
| 7,384,793 B2 | 6/2008 | McCash et al. |
| 7,547,285 B2 | 6/2009 | Kline |
| 7,594,894 B2 | 9/2009 | Cardell et al. |
| 7,631,567 B1 | 12/2009 | Hill |
| 7,779,840 B2 | 8/2010 | Acker et al. |
| 7,897,400 B2 | 3/2011 | Timmins et al. |
| 7,964,389 B2 | 6/2011 | Chen |
| 8,002,712 B2 | 8/2011 | Meka et al. |
| 8,240,187 B2 | 8/2012 | Colman et al. |
| 2002/0134137 A1* | 9/2002 | Ondov ................. G01N 1/2273 73/28.05 |
| 2002/0157621 A1 | 10/2002 | Lefrancois et al. |
| 2003/0153844 A1* | 8/2003 | Smith .................. A61B 10/0051 600/573 |
| 2004/0024330 A1 | 2/2004 | Djupesland et al. |
| 2004/0161804 A1 | 8/2004 | Mccash et al. |
| 2004/0162500 A1 | 8/2004 | Kline |
| 2004/0232052 A1 | 11/2004 | Call et al. |
| 2004/0249300 A1 | 12/2004 | Miller |
| 2005/0065446 A1* | 3/2005 | Talton .................... A61B 5/097 600/529 |
| 2005/0085740 A1 | 4/2005 | Davis et al. |
| 2005/0137491 A1 | 6/2005 | Paz et al. |
| 2006/0195040 A1* | 8/2006 | Nason .................. A61B 5/0803 600/532 |
| 2006/0238757 A1* | 10/2006 | Silcott ............... G01N 15/0618 356/338 |
| 2007/0173731 A1 | 7/2007 | Meka et al. |
| 2007/0199567 A1 | 8/2007 | Kanzer |
| 2007/0235100 A1* | 10/2007 | Tomerlin ............... F16L 11/118 138/112 |
| 2008/0038207 A1 | 2/2008 | Edwards et al. |
| 2008/0214947 A1* | 9/2008 | Hunt ..................... A61B 5/083 600/532 |
| 2009/0187113 A1 | 7/2009 | Friedman et al. |
| 2009/0255535 A1 | 10/2009 | Kanzer |
| 2011/0105856 A1* | 5/2011 | Haines ..................... A61B 5/00 600/300 |
| 2012/0004571 A1 | 1/2012 | Ku et al. |
| 2012/0168634 A1 | 7/2012 | Egen et al. |
| 2012/0203126 A1 | 8/2012 | Kahlman et al. |
| 2016/0022946 A1 | 1/2016 | Sislian et al. |

FOREIGN PATENT DOCUMENTS

| | | |
|---|---|---|
| CN | 101742964 A | 6/2010 |
| CN | 102498398 A | 6/2012 |
| CN | 102596029 A | 7/2012 |
| DE | 19718924 A1 | 10/1998 |
| EP | 0302681 A2 | 2/1989 |
| EP | 2104451 A2 | 9/2009 |
| EP | 2379128 A2 | 10/2011 |
| JP | 0854389 A | 2/1996 |
| JP | 2005538819 A | 12/2005 |
| WO | 2007120644 A2 | 10/2007 |
| WO | 2012006250 A1 | 1/2012 |
| WO | 2014165184 A1 | 10/2014 |

OTHER PUBLICATIONS

Sislian et al., "Bacterial aerosol neutralization by aerodynamic shocks using an impactor system: Experimental results for *E. coli* and analysis", Chemical Engineering Science, Nov. 4, 2009, vol. 65, 1490-1502.

Abouali et al., "A model for supersonic and hypersonic impactors for nanoparticles", Journal of Nanoparticle Research, 2005, 7(1):75-88.

Bao et al., "Microfluidics-Based Lysis of Bacteria and Spores for Detection and Analysis", Principles of Bacterial Detection: Biosensors, Recognition Receptors and Microsystems, 2008, pp. 817-831.

CDC, "Trends in Tuberculosis—United States, 2008", MMWR Weekly, Mar. 20, 2009, 58(10), pp. 249-253.

Conde et al., "Comparison of Sputum Induction with Fiberoptic Bronchoscopy in the Diagnosis of Tuberculosis", Am. J. Respir. Crit. Care Med., 2000, vol. 162, pp. 2238-2240.

Dunlap et al., "Diagnostic Standards and Classification of Tuberculosis in Adults and Children", American Journal of Respiratory and Critical Care Medicine, 2000, 161(4), pp. 1376-1395.

Gupta et al., "Flow dynamics and characterization of a cough", Indoor Air, 2009, vol. I9, pp. 517-525.

Hering et al., "Design and Evaluation of New Low-Pressure Impactor. 2", Environmental Science and Technology, 1979, 13(2):184-188.

Hering et al., "Design and Evaluation of New Low-Pressure Impactor. I.", Environmental Science and Technology, 1978, 12(6):667-673.

Joseph et al., "Breakup of a liquid drop suddenly exposed to a high-speed airstream", International Journal of Multiphase Flow, 1999, 25(6-7):1263-1303.

Keeler et al., "Reducing the global burden of tuberculosis: the contribution of improved diagnostics", Nature Reviews: Diagnostics, 2006, 61006:49-57.

Klevens et al., "Estimating Health Care-Associated Infections and Deaths in U.S. Hospitals, 2002", Public Health Reports, Mar.-Apr. 2007, vol. 122, pp. 160-166.

(56) References Cited

OTHER PUBLICATIONS

Marentis et al., "Microfluidic Sonicator for Real-Time Disruption of Eukaryotic Cells and Bacterial Spores for DNA Analysis", Ultrasound in Medicine and Biology, 2005, 31(9), pp. 1265-1277.

Martens-Habbena et al., "Sensitive Determination of Microbial Growth by Nucleic Acid Staining in Aqueous Suspension", Applied and Environmental Microbiology, 2006, 72(1), pp. 87-95.

Perkins et al., "Facing the Crisis: Improving the Diagnosis of Tuberculosis in the HIV Era", The Journal of Infectious Diseases, 2007, 196(Suppl 1), pp. S15-S27.

Pfyffer et al., "Rapid detection of mycobacteria in clinical specimens by using the automated BACTEC 9000 MB system and comparison wih radiometric and solid-culture systems", Journal of Clinical Microbiology, 1997, 35(9), pp. 2229-2234.

Sakundarno et al., "Insufficient quality of sputum submitted for tuberculosis diagnosis and associated factors, in Klaten district, Indonesia", BMC Pulmonary Medicine, 2009, 9(1), 11 pgs.

Schoch et al., "Diagnostic Yield of Sputum, Induced Sputum, and Bronchoscopy after Radiologic Tuberculosis Screening", Am. J. Respir. Crit. Care Med., 2007, vol. 175, pp. 80-86.

Scott II, "The Direct Medical Costs of Healthcare-Associated Infections in U.S. Hospitals and the Benefits of Prevention", Centers for Disease Control and Prevention, 2009, 16 pgs.

Teshima et al., "Biomechanical effects of shock waves on *Esherichia coli* and phage DNA", Shock Wavers, 1995, vol. 4, pp. 293-297.

Vitko et al., "Sensor Systems for Biological Agent Attacks: Protecting Buildings and Military Bases", The National Academies Press, 2005, 209 pgs.

Weber et al., "Comparison of Hospitalwide Surveillance and Targeted Intensive Care Unit Surveillance of Healthcare-Associated Infections", Infection Control and Hospital Epidemiology, 2007, 28(12), pp. 1361-136613.

Who, "Diagnostics for tuberculosis, Global Demand and market potential", Who, 2006, 205 pgs.

Who, "Global Tuberculosis Control 2009, Epidemiology, Strategy, Financing", Who Report 2009, 314 pgs.

World Health Organization, "Guidance for National Tuberculosis Programmes on the management of tuberculosis in children, Chapter 1 in the Series", Int. J. Tuberc. Lung Dis., 2006, 10(10), pp. 1091-1097.

Extended European Search Report for European Application No. 11804234.0, Search completed Apr. 26, 2017, dated May 8, 2017, 10 Pgs.

Extended European Search Report for European Application No. 14780070.0, Search completed Oct. 12, 2016, dated Oct. 19, 2016, 13 Pgs.

International Preliminary Report on Patentability for International Application PCT/US2011/042854, dated Jan. 8, 2013, 7 Pgs.

International Preliminary Report on Patentability for International Application PCT/US2014/024682, dated Sep. 15, 2015, mailed Sep. 24, 2015, 11 Pgs.

International Search Report and Written Opinion for International Application PCT/US2011/042854, report completed Nov. 1, 2011, dated Nov. 15, 2011, 8 Pgs.

International Search Report and Written Opinion for International Application PCT/US2014/024682, report completed Jul. 10, 2014, dated Aug. 11, 2014, 13 Pgs.

Biswas et al., "The particle trap impactor", Journal of Aerosol Science, vol. 19, No. 1, Feb. 1, 1988, pp. 113-121.

Cash et al., "A Variable Order Runge-Kutta Method for Initial Value Problems with Rapidly Varying Right-Hand Sides", ACM Transactions of Mathematical Software, Sep. 1990, No. 16, No. 3, pp. 201-222.

Clayden et al., "HIV, Hepatitis C Virus (HCV), and Tuberculosis Drugs, Diagnostics, Vaccines, and Preventive Technologies in Development, 2011 Pipeline Report", i-Base/Treatment Action Group, Jul. 2011, 162 pgs. (presented in two parts).

Clift et al., "Bubbles, Drops, and Particles", Academic Press, 1978, 394 pgs. (presented in two parts).

Cunningham et al., "Diagnostics for tuberculosis: global demand and market potential", World Health Organization, 2006, 205 pgs.

Dunlap et al., "Diagnostic Standards and Classification of Tuberculosis in Adults and Children", American Journal of Respiratory and Critical Care Medicine, 2000, vol. 161, pp. 1376-1395.

Fennelly et al., "Cough-generated Aerosols of Mycobacterium tuberculosis", American Journal of Respiratory and Critical Care Medicine, vol. 169, No. 5, Mar. 1, 2004, pp. 604-609, first published on Dec. 4, 2003.

Fennelly et al., "Variability of Infectious Aerosols Produced During Coughing by Patients with Pulmonary Tuberculosis", American Journal of Respiratory and Critical Care Medicine, Sep. 1, 2012, vol. 186, Issue 5, pp. 450-457, first published online on Jul. 12, 2012.

Jones-Lopez et al., "Cough Aerosols of Mycobacterium tuberculosis in the Prediction of Incident Tuberculosis Disease in Household Contacts", Clinical Infectious Diseases, vol. 63, Issue 1, Jul. 1, 2016, pp. 10-20, first published on Mar. 29, 2016.

Lindsley et al., "Measurements of Airborne Influenza Virus in Aerosol Particles from Human Coughs", PLoS ONE, Nov. 2010, vol. 5, Issue 11, pp. e15100-1-e15100-6.

Peres et al., "Comparison of two concentrations of NALC-NaOH for decontamination of sputum for mycobacterial culture", The International Journal of Tuberculosis and Lung Disease, vol. 13, No. 12, Dec. 2009, pp. 1572-1575.

Pratt et al., "Trends in tuberculosis—United States. 2008", Center of Disease Control and Prevention, Mar. 20, 2009, vol. 58, No. 10, pp. 246-253.

Rader et al., "Effect of Ultra-Stokesian Drag and Particle Interception on Impaction Characteristics,", Aerosol Science and Technology, 1985, vol. 4, pp. 141-156.

Scholz et al., "PneumoniaCheck: A Device for Sampling Lower Airway Aerosols", Journal of Medical Devices, Dec. 2010, vol. 4, pp. 041005-1-041005-6.

Stewart, S. L., "Effect of impact stress on microbial recovery on an agar surface", Applied and Environmental Microbiology, vol. 61, No. 4, Apr. 1995, pp. 1232-1239.

Wainwright et al., "Cough-generated aerosols of Pseudomonas aeruginosa and other Gram-negative bacteria from patients with cystic fibrosis", Thorax, Jul. 1, 2009, vol. 64, pp. 926-931.

Who, "Global Tuberculosis Report 2012", Who, 2012, 98 pgs.

Who, "Guidance for National Tuberculosis Programmes on the management of tuberculosis in children, Chapter 1: Introduction and diagnosis of tuberculosis in children", International Journal of Tuberculosis and Lung Disease, 2006, vol. 10, No. 10, pp. 1091-1097.

* cited by examiner

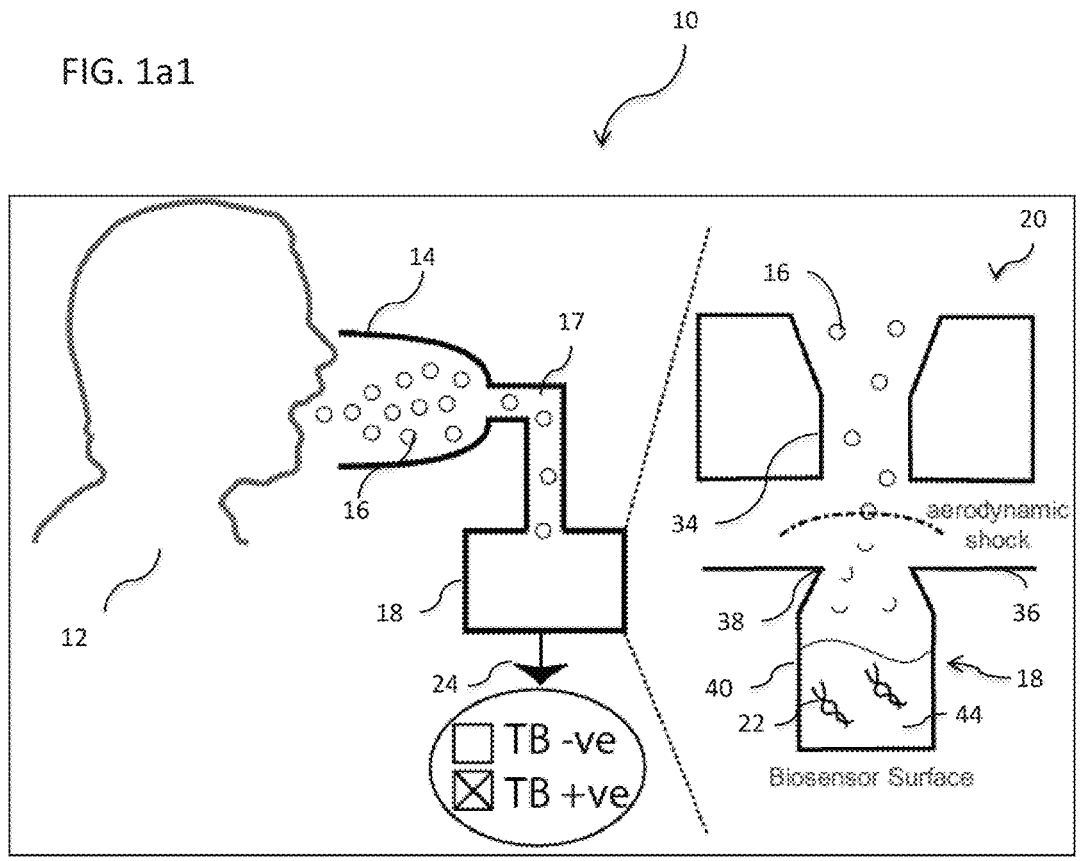
FIG. 1a1

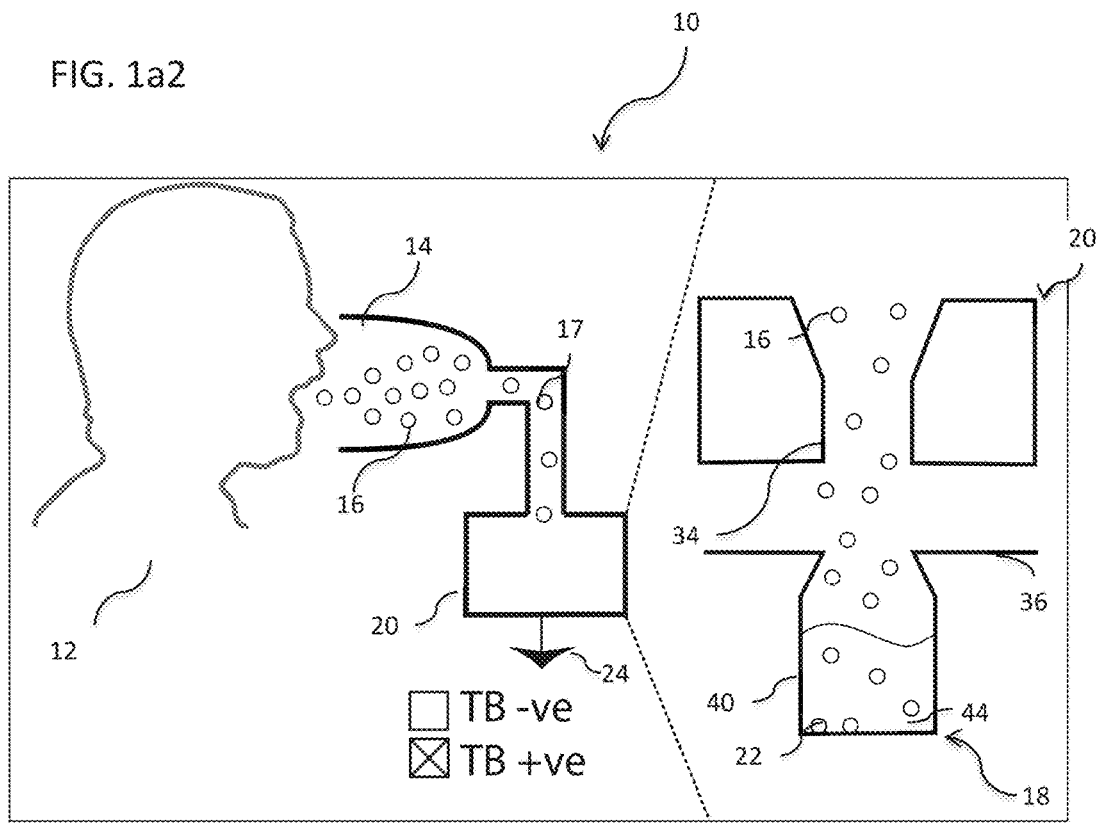
FIG. 1a2

FIG. 3

SYSTEM FOR AIRBORNE BACTERIAL SAMPLE COLLECTION AND ANALYSIS

FIELD OF THE INVENTION

The current invention is directed to a system for collecting and analyzing airborne bacteria or biological particles; and more particularly to a system comprising an aerosol collection system for airborne bacterial or biological particle detection that can be used to prepare a sample for diagnosis or directly diagnose a sample for bacterial infection from the environment or from a patient, such as, for example, tuberculosis.

BACKGROUND OF THE INVENTION

Tuberculosis (TB) is a contagious disease that causes 2 million deaths annually. Approximately 9.3 million people worldwide develop TB every year, of which some estimated 4.4 million are undiagnosed. Improving TB diagnostics would result in approximately 625,000 annually adjusted lives saved worldwide, and elimination of TB from industrialized countries. (See, e.g., Center of Disease Control and Prevention, TB elimination: Trends in tuberculosis 2008, (2009); and World Health Organization, Diagnostics for tuberculosis: global demand and market potential. (2006), the disclosures of each of which are incorporated herein by reference.)

White all common TB diagnostic devices, except X-ray, rely on sputum sample collection. Typically, three samples—more than 3 mL each—are collected per patient. This procedure is particularly difficult in some patient populations. (See, M. B. Conde, et al., *American Journal of Respiratory and Critical Care Medicine,* 162:2238-2240, (2000); and O. D. Schoch, et al., *American Journal of Respiratory and Critical Care Medicine,* 175:80-86, 2006, the disclosures of which are incorporated herein by reference.) For example, in the case of children, special procedures such as sputum induction and gastric aspiration are required; all of which are unpleasant and difficult for both healthcare providers and patients. (World Health Organization, Introduction and diagnosis of tuberculosis in children. *International Journal of Tuberculosis and Lung Disease,* 10(10):10911097, (2006), the disclosure of which is incorporated herein by reference.) In cases where sputum induction is not successful, a procedure known as bronchoalveolar ravage (BALI is performed using fiberoptic bronchoscopy. (N. E. Dunlap, et al., American Journal of Respiratory and Critical. Care Medicine, 161(4):1376-1395, (2000), the disclosure of which is incorporated herein by reference.) The procedure requires a medical doctor and can cause infections if the bronchoscope is not properly disinfected. Moreover, sputum samples are usually contaminated with saliva, which lowers their quality (less *M. tuberculosis* cells per mL) resulting in low diagnostic sensitivities. (M. Sakundarno, et al., *BMC Pulmonary Medicine,* 9(1):16, (2009), the disclosure of which is incorporated herein by reference.)

Each TB diagnostic test is characterized by its practicality and performance. (See, e.g., World Health Organization, Diagnostics for tuberculosis: global demand and market potential. (2006); World Health Organization, *International Journal of Tuberculosis and Lung Disease,* 10(10): 10911097, (2006); and World Health Organization, Global tuberculosis control: Surveillance, planning, financing (2009), the disclosures of each of which are incorporated herein by reference.) Practicality refers to the time, training, resources, accessibility and cost of conducting the test. Performance refers to the sensitivity and specificity of the test. While an ideal diagnostic would be practical with high performance, current TB diagnostics inherently have a trade-off between the two. (See, WHO citations above.) These diagnostics include: radiographic methods, bacteriological culture, drug susceptibility testing culture (DST), sputum smear microscopy (SSM), and nucleic acid amplification test (NAAT). (See, WHO citations above; and M. D. Perkins and J. Cunningham, *The Journal of Infectious Diseases,* 196(Suppl 1):S15-27, (2007), the disclosure of which is incorporated herein by reference.) Radiology (chest X-rays) is one of the fastest diagnostics (<1 hr), but suffers from non-specificity and requires expensive equipment operated in a lab. Bacterial culture is considered the gold standard with 87% sensitivity and can detect as low as 10-100 cells/mL from sputum. Further processing of bacterial culture using DST allows the identification of specific strains of MDR-TB. However, obtaining results takes 2-6 weeks in a resource-intensive tab setting. (See, G. E. Pfyffer, et al., *Journal of Clinical Microbiology,* 35(9):2229-2234, (1997), the disclosure of which is incorporated herein by reference.) SSM is the most practical and widely used test because it is relatively inexpensive and simple. A sputum sample is stained for acid-fastness of *M. tuberculosis*. More than 10,000 cells/mL of sputum are needed for a positive identification by a microscope operator (ss+). (See, WHO, (2006) publication, cited above.) Because of backlog, these tests can take up to 6 months in some countries and require multiple visits. The SSM sensitivity is less than 60% (as low as 20% in high-risk groups) and although the specificity is high in high-prevalence groups it suffers in industrialized countries. (See, M. D. Perkins & J. Cunningham, cited above.) NAAT has a sensitivity >95% for SSM positive patients (ss+) (60-70% for ss−) with high specificity. 10-1000 cells/mL of sputum contain enough DNA to amplify, hybridize and produce a positive signal. (See, M. D. Perkins & J. Cunningham, cited above.) NAAT and bacterial culture have the highest performance and are the only two tests that can detect MDR-TB. NAAT suffers from low practicality due to sputum-based sample preparation by a lab technician and is therefore highly variable in resource-limited labs. (See, M. D. Perkins & J. Cunningham, cited above.) NAAT would satisfy priorities of developing and industrialized countries if sample preparation methods were cost-effectively automated.

Another diagnostic issue that is challenging the medical community involves hospital-acquired infections (HAIs). According to the Centers for Disease Control and Prevention (CDC), 1.7 million (9.3 per 1,000 patient-days or 4.5 per 100 admissions) annual HAIs occur in U.S. hospitals causing some 99,000 deaths a year. (See, e.g., R. M. Klevens, at al., *Public Health Reports,* 122, (2007), the disclosure of which is incorporated herein by reference.) In turn, it is estimated that HAIs correspond to annual medical costs exceeding $35 billion. (See, R. D Scott II, *Centers for Disease Control and Prevention,* 2009, the disclosure of which is incorporated herein by reference.) More and more it is being recognized that HAIs are a serious problem, both from a public health standpoint, and from the perspective of cost-containment for medical expenses.

There are three different routes of transmission for these diseases: touch, droplet, and airborne. Both droplet and airborne transmissions require the formation of an aerosol that can be inhaled to cause infections. For example, one of the most common inhaled infections is pneumonia. Moreover, while hospital acquired pneumonia (HAP) accounts for 11-15% of all HAIs, it causes a disproportionate 36% of deaths. Indeed, some 79% of HAP infections are non-device related and more than 80% are bacterial. (See, D. J. Weber, et al., *Infection Control and Hospital Epidemiology,* 28(12): 1361-1366, (2007), the disclosure of which is incorporated herein by reference.) From this it can be estimated that nearly 160,000 HAIs and 23,000 deaths are caused by inhalation of aerosol bacteria (specifically *S. pneumoniae*). Furthermore, TB, and multidrug-resistant tuberculosis (MDR-TB) have also surfaced causing further problems in aerosol transmission in hospitals. (See, S. K. Sharma and A. Mohan, *Chest,* 130(1):261-272, (2006), the disclosure of which is incorporated herein by reference.)

Bacterial aerosol collectors/analyzers that can diagnose contaminants, either directly from a patient or in the atmosphere, have the potential to provide warnings of these infectious agents, and, thereby avoid further infection. However, a key challenge to providing a detector system with sufficient sensitivity is to collect and rapidly amplify the low-concentrations of bacterial aerosol by delivering highly concentrated analyte (such as DNA) to sensors. Conventional sensors simply do not meet the requirements needed to provide direct diagnostic of possible infection or contamination risks from aerosol sources, such as a patient's breath, cough or sneeze, or from the environment. Accordingly, a need exists to provide a bacterial and or biological collector/analyzer for detecting possible sources of infection directly from a patient and/or contamination from airborne bacterial sources.

SUMMARY OF THE INVENTION

The current invention is directed to an aerosol bacterial and or biological collector/analyzer for the diagnosis of respiratory tract infections in patients or contaminants in the atmosphere.

In one embodiment, the aerosol collection and analysis system includes:
  a patient interface defining a fluid path, where a first end is capable of engaging the patient such that at least a portion of the outflow of breath from the patient is captured by the interface as a gaseous sample;
  an interconnecting tube interconnecting the interface and an impactor;
  an aerodynamic impactor defining a fluid path between the interconnecting tube and the collection vessel, where the aerodynamic impactor applies inertial force differences between the gaseous sample and the biological particulates suspended in said sample to collect these biological particulates in one of either an intact or lysed state, thereof;
  a collection vessel connected with the impactor containing a liquid medium for preserving the biological particulates from the gaseous sample; and
  a pump for creating a flow pressure from the first end of the interface to the collection vessel such that the gaseous sample is urged through the fluid path defined by the interconnecting tube and impactor into the collection vessel.

Wherein in an embodiment where a sufficient inertial force is applied to the biological particulates to lyse the particulates, the internal components of the lysed biological particulates, such as, for example, DNA, are released.

In another embodiment, the interface comprises a full-face constant positive airway pressure mask.

In still another embodiment, the interconnecting tube includes at least one auxiliary compensating inlet disposed traverse to the axis of the interconnecting tube providing an outlet to the atmosphere. In one such embodiment, the at least one auxiliary compensating inlet is disposed at an angle to the interconnecting tube of greater than 90 degrees. In still another such embodiment, a filler is disposed at the outlet of the auxiliary compensating inlet. In yet another such embodiment, the filler is a high-efficiency particulate air (HEPA) filter.

In yet another embodiment, the impactor includes a converging nozzle defining the fluid path of the impactor, and a flat collection surface disposed distal to said converging nozzle and perpendicular to the flow path. In such an embodiment, the flat collection surface has an inlet orifice disposed therein and aligned with the fluid path of the converging nozzle. In another such embodiment, the sample pressure downstream ($P_1$) of the nozzle and the sample pressure upstream ($P_0$) of the nozzle follow the inequality $P_1/P_0<0.53$. In still another such embodiment, the distance from the nozzle to the collection surface (x), and the diameter of the nozzle (d) have the following ratio $x/d=1.2$. In yet another embodiment, the x/d ratio is made variable. In yet another such embodiment, the sample-facing surface of the nozzle is mirror polished.

In still yet another embodiment, the collection vessel tapers toward the second end outlet.

In still yet another embodiment, the outlet may be accessed without opening any other portion of the collection vessel. In one such embodiment, the outlet may be accessed via a syringe.

In still yet another embodiment, the distance between the first end of the collection vessel and the surface of the liquid medium is approximately 4 mm.

In still yet another embodiment, the system further includes a sensor capable of detecting DNA from the lysed sample, the sensor being disposed in fluid connection with the second end of the collection vessel.

In still yet another embodiment, the system further includes a sensor capable of detecting intact bacteria, the sensor being disposed in fluid connection with the second end of the collection vessel.

In still yet another embodiment, the interconnections between the components of the system comprise quick-disconnect couplings having valves such that once disconnected the valves automatically close.

In still yet another embodiment, the components of the system are autoclavable.

In still yet another embodiment, the components of the system are resistant to common sterilization chemicals.

In still yet another embodiment, the sample facing surfaces of the system are formed from a plastic material.

In still yet another embodiment, the sample is formed by a method selected from breathing, coughing and sneezing.

In still yet another embodiment, the liquid medium is a buffer.

In another embodiment the invention is directed to a method of collecting and analyzing an aerosol sample for bacterial infection including:
  collecting the outflow from a patient as a sample;
  transporting the sample to an impactor;
  applying an inertial force to the sample to either separate an biological particulates therein from the sample, or to lyse any bacterial particulates therein to release the internal components of the cells; and
  collecting either the intact particles or the internal components of the lysed particulates in a fluid medium for analysis.

In still another embodiment, the method includes compensating the pressure of the system for the oscillating outflow from the patient.

In yet another embodiment, the method includes analyzing the internal components of the cells for bacterial contaminants in real-time.

In still yet another embodiment, the method includes withdrawing a batch sample of the internal components from the fluid medium for analysis without having to disassemble the system.

BRIEF DESCRIPTION OF THE DRAWINGS

These and other features and advantages of the present invention will be better understood by reference to the following detailed description when considered in conjunction with the accompanying data and figures, wherein:

FIGS. 1a1 and 1a2 provide schematics of embodiments of an aerosol biological collector/analyzer system in accordance with the current invention;

FIG. 3 provides a schematic of an embodiment of an aerosol biological collector/analyzer system in accordance with the current invention;

DETAILED DESCRIPTION OF THE INVENTION

Figure 1B:
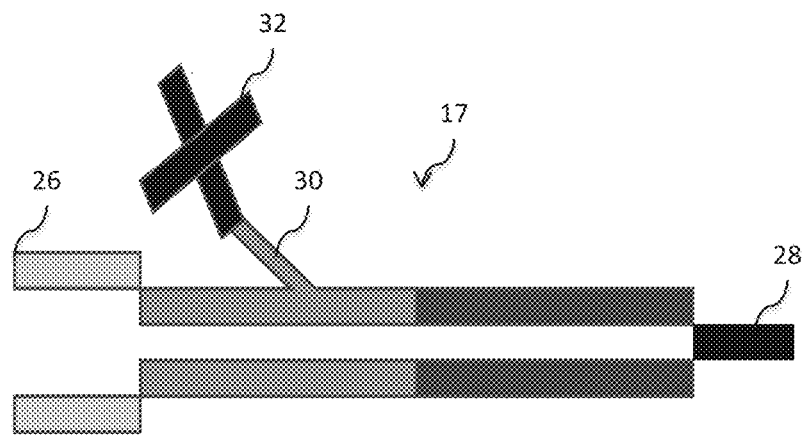
FIGS. 1b and 1c provide schematics of embodiments of a component of an aerosol biological collector/analyzer system in accordance with the current invention.

The current invention is directed to an aerosol biological collector/analyzer system. In particular, the current invention is directed to an airborne aerosol collection and bacterial analysis system, capable of collecting an airborne aerosol sample and preparing it for analysis via aerodynamic shock in a single-step.

A schematic of one embodiment of the aerosol collection and analysis system (10) of the instant invention is schematically depicted in FIGS. 1a1 and 1a2. As shown, a patient (12) wears a mask or other patient interface (14) and breathes, coughs, or sneezes regularly. As the aerosol droplets (16), which are typically on the order of 1-12 μm, are produced by the patient, they are transported via an interconnecting tube (17) to a collector (18), and simultaneously either separated intact (as shown in FIG. 1a2) from the sample or lysed via an aerodynamic impactor (20) (as shown in FIG. 1a1). The exposed cellular DNA and or intact biological particles (22) are then either collected in a suitable medium, or directly detected by a sensor (24) producing either a positive or negative reading.

In summary, the aerosol biological collector/analyzer system of the current invention includes four basic components, including: the patient/biosensor interface (14), which includes a device capable of engaging the patient and collecting substantially all the airflow from the patient; a device for interconnecting (17) the patient/sensor interface with the impactor, which includes tubing filters, flow regulators, etc. capable of both providing an interconnection between the components and balancing the naturally oscillating input flow-rate from patient with the constant flow-rate of the pump; an impactor (20), which includes a nozzle, impactor plate, collection tube, etc. capable of separating and/or lysing the cells of any bacteria suspended in the collected sample from the patient; and a pump (not shown), which includes all necessary tubing, filters, flow regulators, etc. capable of providing a steady and sufficient flow-rate through the apparatus to the patient/biosensor interface. Although the following will describe alternative embodiments of each of the components of the biosensor system of the invention, it will be understood that these alternative embodiments are merely provided as examples, and that one of ordinary skill in the art will appreciate other modifications and alternatives to the basic aerosol biological collector/analyzer system without departing form the scope of the current invention.

With regard to the system/patient interface (14), although any device capable of providing an interconnection between the patient and the aerosol biological collector/analyzer system to collect natural breath samples may be used, such as, for example, a simple tube, in a preferred embodiment an interface designed to fit securely and fully over a patient's nose and mouth is preferred. Such a secure interface is preferable both because it allows for the patient to cough and breathe regularly during testing, but also because it prevents external atmospheric contaminates from entering the system during testing (which can lead to detection of environmental bacteria), and simultaneously prevents potential infectious agents emitted from the patient from escaping the system (which leads to system losses and loss in sensitivity and can cause infection of other patients or healthcare professionals). In one such embodiment, the interface would comprise a full-face CPAP (Constant Positive Airway Pressure) mask, such as, for example, the ComfortGel Full® from Phillips Respironics. Although not required, preferably such masks would be disposable to reduce the chances of contamination before and after use.

With regard to the interconnection (17), it should be understood that any device capable of providing suitable fluid communication between the patient/biosensor interface (14) and the impactor (20), such as, for example, a simple length of tubing, may be used in the current invention. However, in one embodiment, a device capable of balancing the naturally oscillating input flow-rate from the patient with the constant flow-rate of the pump is provided between the patient/biosensor interface and the impactor. An exemplary embodiment of such a device is shown schematically in FIGS. 1b and 1c. As shown, in this embodiment, the interconnection (17) generally comprises a connector (26) at one end of the interconnection for engaging an opening of the interface (14), and a connector (28) at a second end of the interconnection for engaging the impactor (20). Preferably, the connectors include a through-wall-plug that contains autoclavable or sterile O-rings. In this embodiment, the compensation device includes an auxiliary or flow compensating opening (30) along its length with a filtered (32) opening at the distal end thereof for providing filtered air intake. Any suitable filler may be provided, such as, for example, a HEPA filler.

Figure 1C:
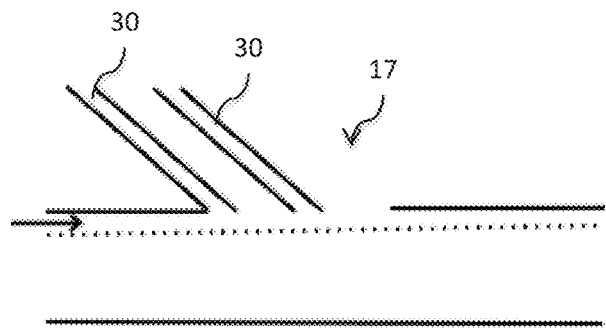

Although this connection may take any suitable form, in an exemplary embodiment the auxiliary compensating opening includes a tee connection, such as a Wye connection, that is angled in relation to the main interconnection at an angle of greater than 90 degrees. The angled design of the compensating tube is provided to minimize aerosol particle losses by having the airflow divert more 90 degrees as it exits through the fillers. The bend in the compensating tube prevents the particles from following the airstream because of the inertial forces on the fluids. Although only a single compensating opening (30) is shown in FIG. 1b, as shown in FIG. 1c the opening can consist of one or multiple side tubes of various diameters connected to multiple HEPA fillers to ensure sufficient flow-rate for the particular application.

Figure 1D:
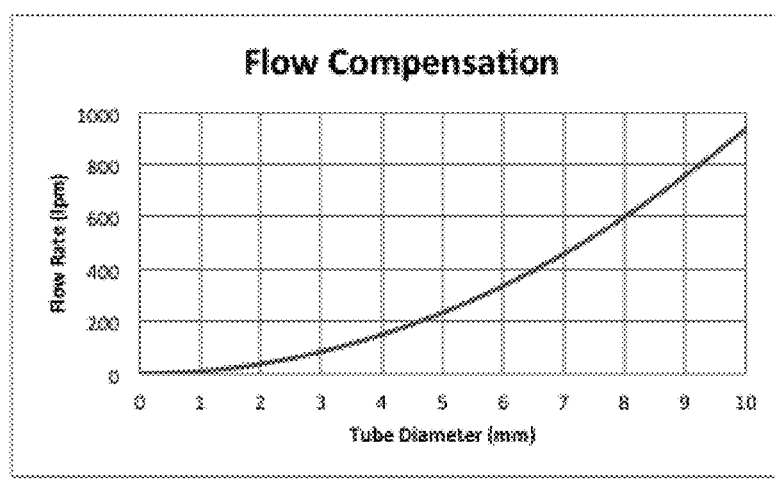
FIG. 1d provides a data graph showing flow rate compensation studies for an embodiment of an aerosol biological collector/analyzer system in accordance with the current invention.

Row compensation through this compensating opening is important. FIG. 1d and Table 1, below, show the maximum flow-rates (or critical flow-rates) that can be compensated given a specific compensating opening diameter. The diameter is determined by the patient peak flow rate during coughing. The calculations summarized in the FIG. 1d and the table are calculated under the assumption of zero pressure drop across the tubes.

TABLE 1

Flow Compensation Parameters

| Example No. | Diameter (mm) | Row-rate (lpm) |
|---|---|---|
| 1 | 0.5 | 2.33 |
| 2 | 1 | 9.35 |
| 3 | 1.5 | 21.04 |
| 4 | 2 | 37.40 |
| 5 | 2.5 | 58.45 |
| 6 | 3 | 84.16 |
| 7 | 3.5 | 114.56 |
| 8 | 4 | 149.63 |
| 9 | 4.5 | 189.38 |
| 10 | 5 | 233.80 |

As an example, providing a compensating opening comprising five side tubes at a 135 degree angle of 5 mm diameter can maintain a flow-rate of 1000 lpm. This flow-rate represents conservative peak flow-rates during a cough. Peak flow rates in male patients of up to 300 lpm during coughing have been seen. (See, e.g., Gupta J K, Indoor Air, 9:517-525 (2009), the disclosure of which is incorporated herein by reference.) Under such a system, the particle loss through the side tubes can be calculated and is 16.5%, however, the other 84.5% of particles are carried in an airstream of 1 lpm to the impactor. This results in a 1000-fold increase in particle concentration carried to the impactor with minimal loss.

Accordingly, the presence of this compensating opening has a major impact on possible flow-rates, and on the operation of the device. While inhaling and exhaling, the compensating opening will equilibrate the flow through the HEPA filter opening (32). In contrast, while a patient is coughing the compensating opening allows the system to rid itself of the excess flow-rate. Accordingly, placing such a compensating opening before the impactor allows for the compensation of the fluid flow-rate between the patient and the impactor with HEPA filtered air, increasing the possible flow-rate of the system substantially. Moreover, having the HEPA filters allows for the avoidance of contamination from the outside in and inside out.

Figure 1E:
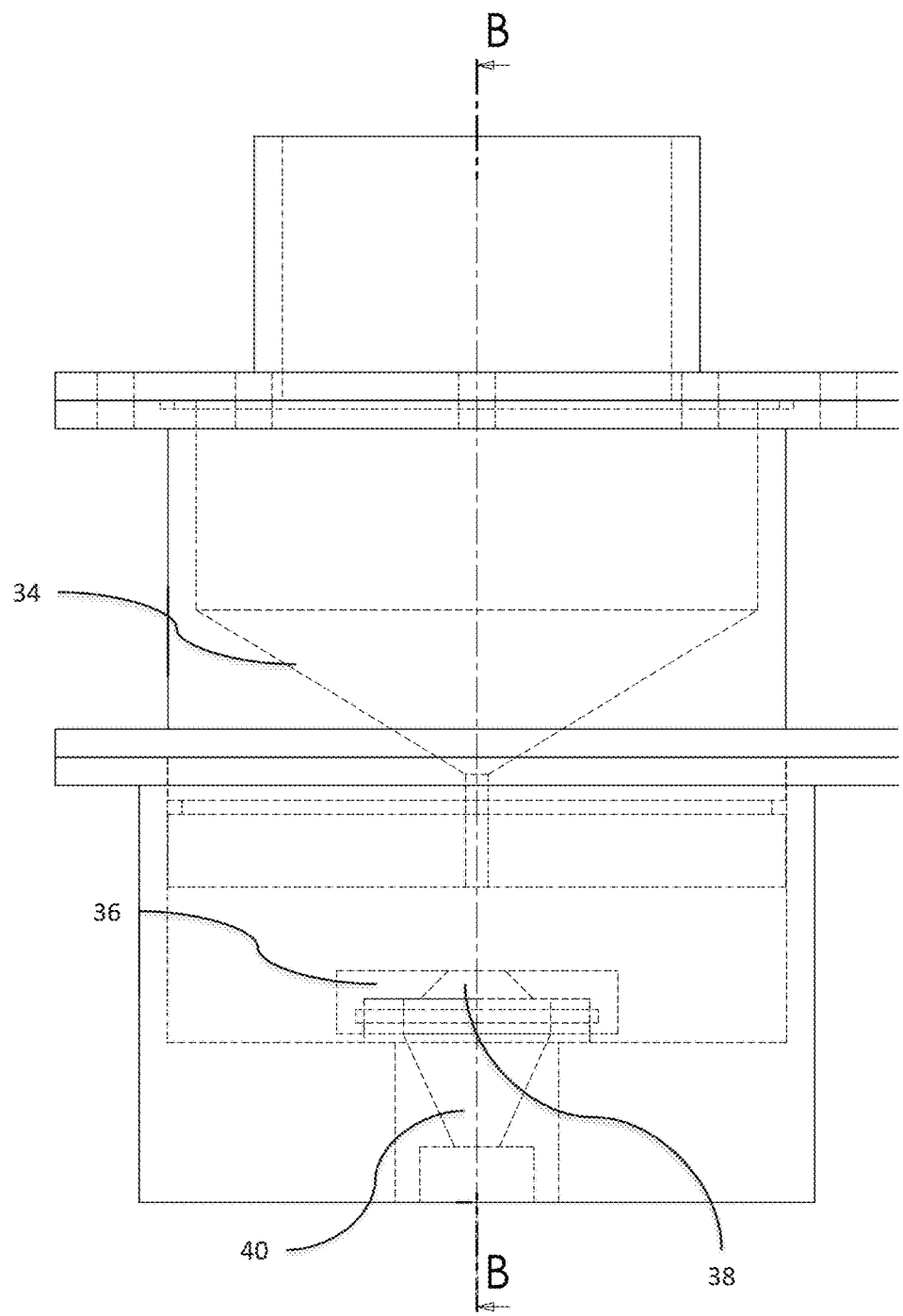
FIGS. 1e and 1f provide schematics of an embodiment of an impactor system in accordance with the current invention, where 1e shows a schematic view of the impactor, and 1f shows a cross section along axis "B" in FIG. 1e.
Figure 1F:
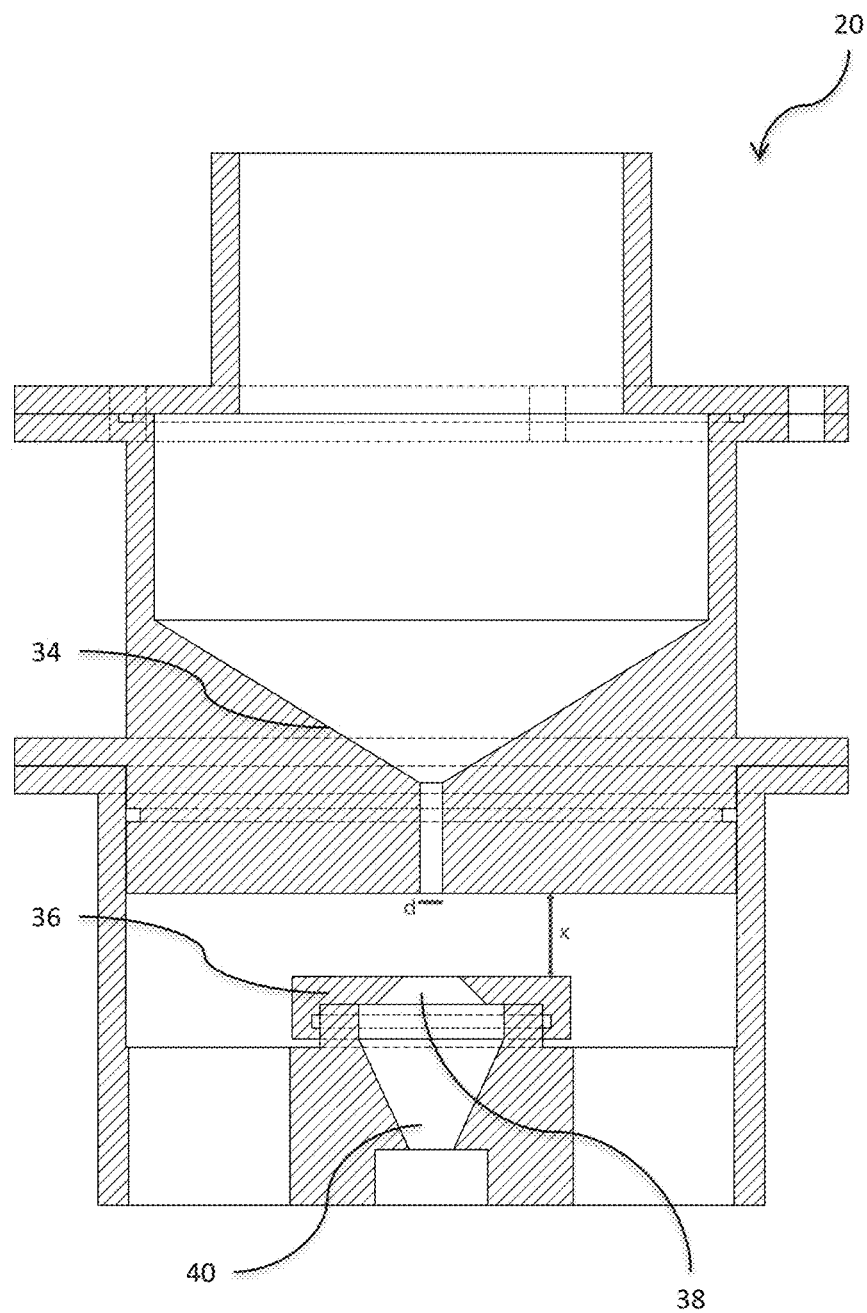

One of the unique features of the system of the instant invention is that it consists of an impactor system (20), which can both collect intact cells and/or lyse cells. That is, the impactor system is capable of passing bacterial cells in air through a shock and either separating them from the gaseous sample intact, or lysing the cells and collecting fragments, simultaneously. However, the DNA itself does not fragment with one pass through the shock. (See, e.g., K. Teshima, et al., Shock Waves, 4(6):293-297, (1995), the disclosure of which is incorporated herein by reference.) Although any suitable aerodynamic impactor capable of both passing bacterial particulates, such as, for example, cells intact and/or generating shockwaves sufficient to lyse bacterial cells may be used with the biosensor of the instant invention, in one embodiment, as shown in FIGS. 1e and 1f, the impactor (20) consists generally of a converging nozzle (34) through which the aerosol flows perpendicular to a collection surface (36) with an orifice (38) leading to the collection reservoir (40).

In such an impactor system, an aerodynamic shock sufficient to lyse cells is created by operating the impactor nozzle at sonic velocity when $\chi=P_1/P_0<0.53$ (where, $P_1$ is the pressure downstream and $P_0$ is the pressure upstream of the nozzle). Recent computational and experimental studies have shown that E. coli bacteria passing through an aerodynamic shock of this magnitude reach critical decelerations, which causes their break-up. (See, Example 2, below, and P. R. Sislian, et al., Chemical Engineering Science, 64(9):1953-1967, (2009) & P. R. Sislian, et al., Chemical Engineering Science, 65(4):1490-1502, (2010), the disclosures of each of which are incorporated herein by reference.) These studies show that, operating at these conditions, more than 90% of cells are broken up to spill their internal components for subsequent collection or detection, allowing for the collection and preparation of the bacterial aerosol samples in a single step. In addition, the simultaneous break-up and collection in one device eliminates the need to build microfluidic components for cell lysis, greatly simplifying the device.

Although each of the components of the impactor may take a form such that the combination of elements is capable of producing a suitably strong shock in the aerosol sample to lyse any bacterial cells produced by the patient. In particular, the impactor should be provided with a nozzle (34) that creates the impinging flow necessary for inertial particle collection. In turn, the nozzle should preferably be positioned in relation to the orifice (38) of the collection stage such that the components meet the dimensional requirement: x/d=1.2, where x is the distance from the nozzle exit to the collection tube entrance, and d is the diameter of the nozzle exit. Moreover, the nozzle and orifice need to be perfectly aligned and have a tolerance of at least 1%. To reduce air-flow friction, the nozzle may be mirror-polished.

As described above, and shown schematically in FIGS. 1a1 and 1a2, during the operation of the system of the current invention the aerosol (16) entering the impactor (20) flows through the converging nozzle (34), perpendicular to the collection surface (36), and then through the orifice (38) through which the intact or shocked bacteria (22) enters the collection liquid (44). The DNA is collected in a buffer that feeds into post-lysis steps in a sensor system.

Although any sample collector (18) suitable for gathering a sample for either direct or later analysis may be integrated with the impactor (20), preferably the collector is designed to both contain a buffer medium for preserving the sample and also to decelerate the sample bacterial particles before collection. In one embodiment, for example, the collector has the following features:

An outlet in the collector chamber that allows for direct connection of the collection chamber such that exposure to the external environment is avoided. By such a means the collection chamber may easily connect to a sample extractor for easy extraction of the sample without having to disassemble the impactor. This allows for both inline measurements (continuous measurement) and easy offline measurement (or batch measurement). Such a design enables batch collection, but can also be replaced by a continuous pumping system that leads to a detector system. In one such embodiment, the sample extractor consists of a sterile syringe.

A collection chamber that is slanted toward the outlet to allow the entire sample to be removed from the collector.

The collector reservoir should have a volume and be dimensioned such that when filled the distance from the surface of the sample collection medium to the orifice/inlet of the collector is preferably ~4 mm. Simulations indicate that the bacterial particles will be collected at less than 10 m/s at 4 mm clearance from the entrance of the tube to the liquid collection surface, dramatically reducing the kill rate of any bacteria in the sample.

Although suitable collection media are well-known in the art, such as, for example, Phosphate Buffered Saline (PBS) buffer, and may be used in conjunction with the current invention, it will be understood that the instant invention also allows for the integration of a real-time sensor, such as, for example, Fluidigm's Access Array™ System and others, which can identify DNA from internal components specific to a particular bacteria, such as, for example, *M. tuberculosis* bacterium. Such sensors can be integrated with the collection module described above to provide real-time sensing of bacteria, or other biological components of the respiratory tract.

The above discussion has not focused on the materials to be used in constructing the aerosol biological collector/analyzer system of the instant invention. It will be understood that preferably, the device should be isolated from the external environment, and so designed to avoid external contamination, which can lead to detection of environmental bacteria, and also to avoid sample leakage, which can lead to system losses and loss in sensitivity, and which can also lead to spread of disease. For example, the use of quick-disconnect couplings, such as, for example, an Acetal® Quick-Disconnect Coupling Plug, with valves on both plug and socket between components, would allow the lower chamber of the impactor to be isolated both before and after use. Such an arrangement would reduce contamination both from the outside in and inside out, and is preferred to help control contamination before and after use.

In addition, the device should be contamination free, and therefore should be designed to withstand standard disinfection apparatus used on other medical devices. Accordingly, all materials chosen should be autoclavable or should be purchased sterile. Moreover, to minimize the loss of sample, the electrostatic properties of the materials used should be evaluated to avoid collecting charged biological aerosol. In particular, since bacteria are usually negatively charged particles, plastics that do not hold static charges would be a preferred material for parts that might interact with the sample.

Figure 6:
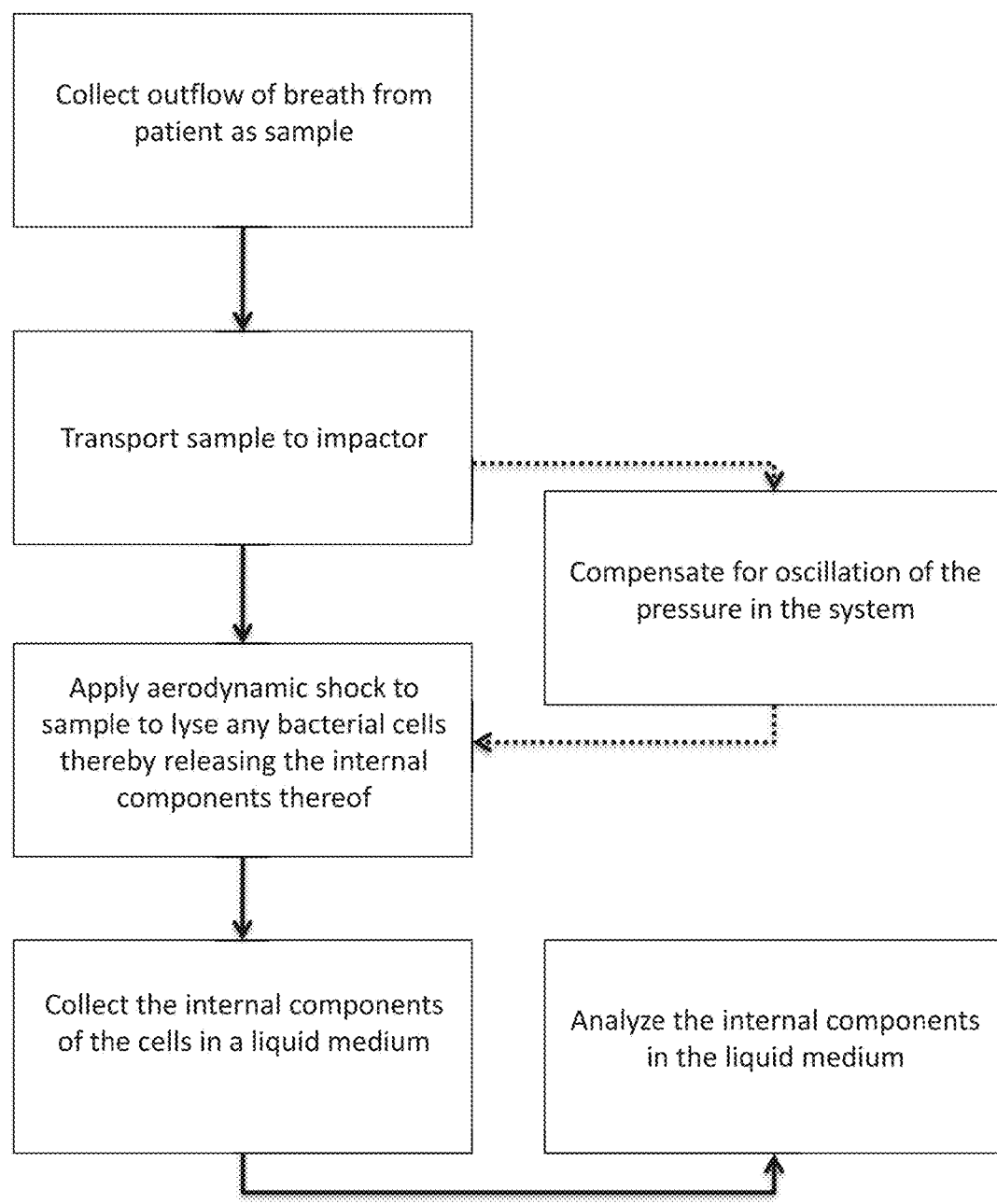
FIG. 6 provides a flow-chart of a method of detecting and analyzing an aerosol sample for bacterial infection in accordance with an embodiment of the current invention

Although the above discussion has focused on an aerosol biological collector/analyzer system for analyzing aerosol samples, the current invention is also directed to a method of analyzing aerosol samples. As shown in the flow-chart in FIG. 6, the method includes the general steps of:

Collecting the outflow of breath, including any coughs or sneezes, from a patient as a sample;

Transporting the sample to an impactor;

Applying an inertial force to the sample to separate any biological particulates from the sample and/or to lyse any bacterial cells contained therein, thereby releasing any internal components therein; and Collecting the intact particulates and/or internal components in a liquid medium for later analysis.

Although these are the basic steps in the process, it should be understood that other steps may be included to comport with the operation of the device described in the above discussion. For example, in one embodiment, the method would also include compensating the system pressure for the natural oscillation in the out and inflow of breath from the patient, and from any over-pressures caused by coughs and/or sneezes.

In terms of the analysis itself, the analysis could be done via a batch method, by withdrawing individual samples from the liquid medium. Alternatively, the analysis could be accomplished in real-time by interconnecting an analyzer in-line with the liquid medium.

EXEMPLARY EMBODIMENTS

In this section several examples of how aerosol biological collector/analyzer systems operate or could be implemented are provided. In addition, a comparison of the performance of an aerosol biological collector/analyzer system made in accordance with the current invention versus a conventional system is provided. The person skilled in the art will recognize that additional embodiments according to the invention are contemplated as being within the scope of the foregoing generic disclosure, and no disclaimer is in any way intended by the foregoing, non-limiting examples.

Example 1: Comparison of Performance with Conventional. Systems—Environmental Sampling Turning to a comparison of the operation of the instant invention with that of a conventional aerosol collection and analysis system, it should be understood at the outset that access to the internal components (ICs) of cells, mainly DNA, is necessary for most detection methods. (See, e.g., N. Bao and C. Lu., *Principles of Bacterial Detection: Biosensors, Recognition Receptors and Microsystems*, pages 817-831. Springer, (2008), the disclosure of which is incorporated herein by reference.) In conventional biosensor systems, as shown in a block-diagram in FIG. 2a, the bacterial aerosol is first collected in a first unit (46), and then lysed (48) in a second unit by either mechanical, heat, chemical, electrical, or laser systems. The lysis products are then purified in subsequent units (not shown) to deliver the target molecules to a suitable sensor. (For FIGS. 2a and 2b it should be noted that the shaded area indicates the liquid medium used to transport the analyte to the sensor, and the oval and helical shapes represent intact bacteria and released DNA, respectively. It should also be noted that in the inventive system the DNA release happens in air.)

In short, existing systems (FIG. 2a) require two separate and disconnected units: a collector (such as a cyclone), and an extractor (such as a sonicator). In contrast, the aerosol biological collector/analyzer system of the instant invention (shown in a block-diagram in FIG. 2b) delivers lysed products directly to the purification units (not shown) of existing systems by breaking cells in air and simultaneously collecting their ICs or DNA in a single-unit (50), but multi-step process. In other words, the two processes (collection & lysis) occur in a single-step via the novel collection/impactor system.

Figure 2A:
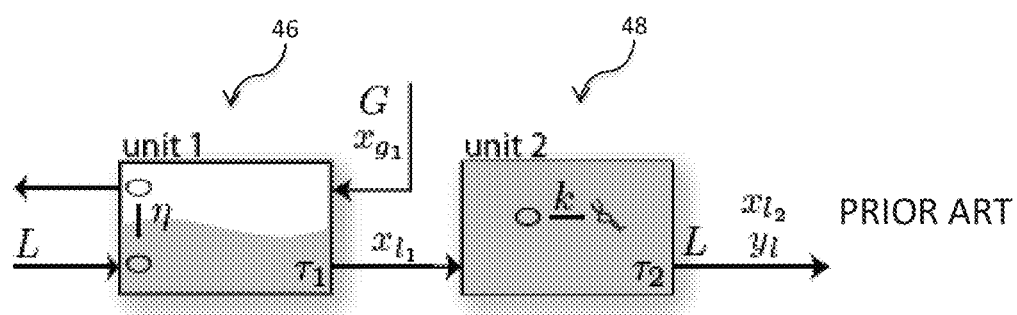
FIGS. 2a and 2b provide block-diagrams of: (a) an existing aerosol biosensor for airborne bacterial detection; and (b) an embodiment of an aerosol biological collector/analyzer system in accordance with the current invention.

The goal in both cases is to detect changes in the concentration of airborne S. pneumoniae ($x_{g1}$) through a fast and concentrated release of cellular DNA ($y_l$). The dynamics of the processes required for the method shown in FIG. 2a are described by the following three differential equations (ODEs):

$$\tau_1 \frac{\partial x_{l1}}{\partial t} = -x_{l1} + \left(\frac{G}{L}\eta\right)x_{g1} \quad [\text{EQ. 1}]$$

$$\tau_2 \frac{\partial x_{l2}}{\partial t} = -(k\tau_2 + 1)x_{l2} + x_{l1}$$

$$\tau_2 \frac{\partial y_l}{\partial t} = -y_l + (k\tau_2)x_{l2}$$

where G and L are the gas and liquid sampling flow-rates, respectively; the subscripts g and l refer to gas and liquid phases, respectively; x is the number concentration of bacteria; $y_l$ is the number concentration of DNA that feeds to purification steps (not shown in FIG. 2); r is the residence time in each process (dead volume divided by L) and η is the collection efficiency of the air sampler.

A number of assumptions have been made in this calculation. For example, it is assumed for the purposes of this calculation that there is one DNA molecule per cell. All concentrations are normalized (non-dimensional) relative to a critical concentration of bacteria in air that will cause infection (i.e., $x_{g1}>1$ causes infection). The break-up of cells is assumed to be a first order reaction in a continuous stirred tank reactor (CSTR) with a reaction constant k. (See, e.g., J. A. Asenjo. *Separation Processes in Biotechnology*. Marcel. Dekker, New York, 1st edition, (1990), the disclosure of which is incorporated herein by reference.)

Figure 3:
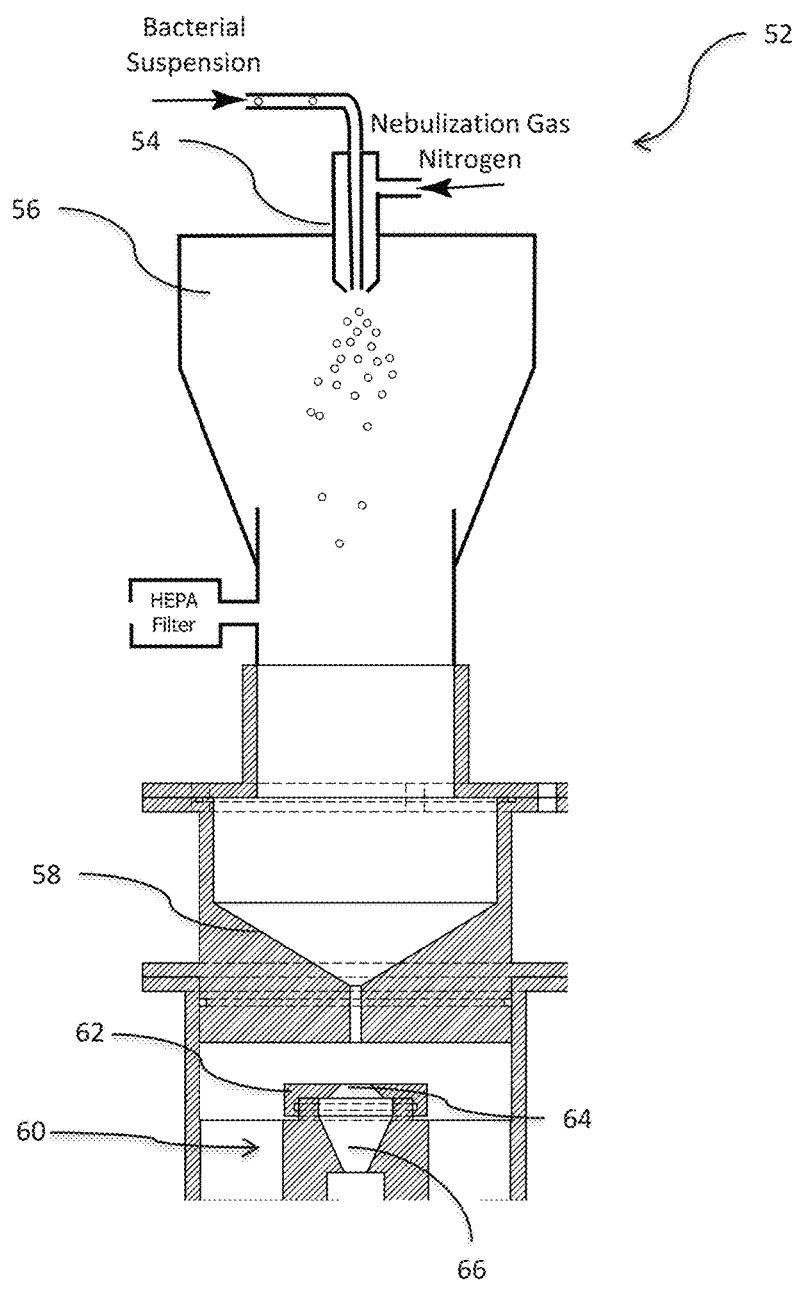

The system (52) used in the experiments is shown schematically in FIG. 3 has the same basic parts described above, and generally consists of a Meinhard nebulizer (54) with a concentric nozzle mixing a liquid bacterial suspension feed and a dispersion gas (N2), a nebulization chamber (56) to collect large droplets, a converging nozzle (58) with an exit diameter of d=0.5 mm through which gas flows perpendicular to a collection plate (60). The collection plate itself is formed from a flat surface (62) with an 0.5 mm orifice (64) leading to the collection reservoir (66). Although not essential, in this embodiment, the impactor also comprises spacers and supports that allow variation of the plate (60) to nozzle (58) distances (x) to vary from 0 to 2 mm (see FIG. 3, inset). As before, the DNA is collected in a buffer that feeds into post-lysis steps in a sensor system that may be separate or integrated.

Finally, system dynamics for the inventive system is expressed as follows:

$$\tau_1 \frac{\partial y_l}{\partial t} = -y_l + \left[\frac{G}{L}\eta_d(1-f)\right]x_{g1} \quad [\text{EQ. 2}]$$

where f is the fraction of cells that remain intact and $\eta_d$ is the collection efficiency of DNA from air. In the gas phase dead volume is approximately 0. Therefore, the break-up is a steady state process that decreases the response time of inventive system. This enhances the theoretical response of the system. EQs. 1 & 2 are of the form z'=Az+Bw, where w and z are a time-dependent input and output, respectively.

Table 2, below provides a set of parameters used in simulations of EQ. 1 and EQ. 2. For the system in FIG. 2a, the extractor is a microfluidic sonicator that can lyse 50% of cells in 30 sec. (See, T. C. Marentis, et al., *Ultrasound in Medicine and Biology*, 31(9):1265-1277, (2005), the disclosure of which is incorporated herein by reference.) $V_1$ and $V_2$ are the dead volumes in unit 1 and unit 2 of FIG. 2a, respectively. It will be understood that for the inventive system (FIG. 2b), there is only one dead volume. (See, W. Martens-Habbena and H. Sass, *Applied and Environmental Microbiology*, 72(1):87-95, (2006), the disclosure of which is incorporated herein by reference.)

TABLE 2

Summary of System Parameters

Figure 2B:
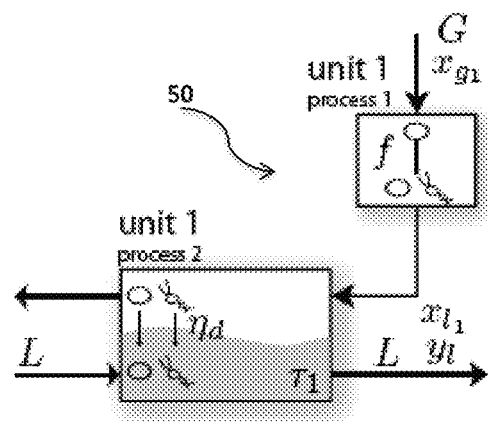

| System | G (L/min) | η | $\eta_d$ | f | L (L/min) | $V_1$ (μL) | $V_2$ (μL) | K (s$^{-1}$) |
|---|---|---|---|---|---|---|---|---|
| FIG. 2a | 325 | 0.9 | — | — | 0.01 | 500 | 500 | 1.38 |
| FIG. 2b | 325 | — | 0.9 | 0.05 | 0.01 | 500 | — | — |

MATLAB® code was used for assessing the time response ($y_l(t)$) of the existing systems (FIG. 2a, EQ. 1), and the inventive system (FIG. 2b, EQ. 2). In order to theoretically evaluate the magnitude of improvement offered by the inventive system, parameter values were selected for the existing systems that yield the best-case operation (as detailed in Table 2, above), rather than parameter values reported for a single existing system or averaging parameter values across many existing systems. (See, e.g., T. C. Marentis, et al. & W. Martens-Habbena and H. Sass, cited above.) FIG. 4 provides data plots showing the theoretical response of conventional systems and the inventive system given a step input (a), and a pulse input (b). (The solid line demonstrates the conventional system with parameters while the dashed lines show response curves of the inventive system portraying three scenarios of $G\eta_d$.)

Figure 4A:
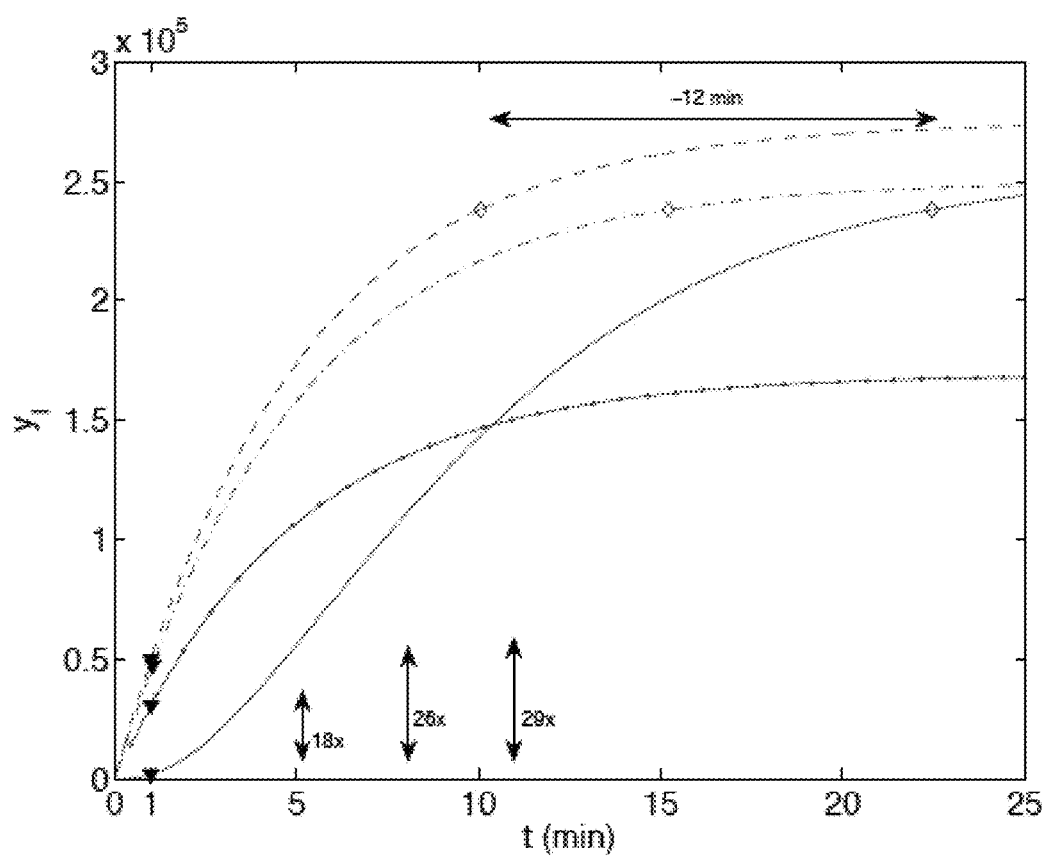
FIGS. 4a and 4b provide data graphs showing the theoretical response of conventional systems and the inventive system given a step input (a), and a puke input (b)
Figure 4B:
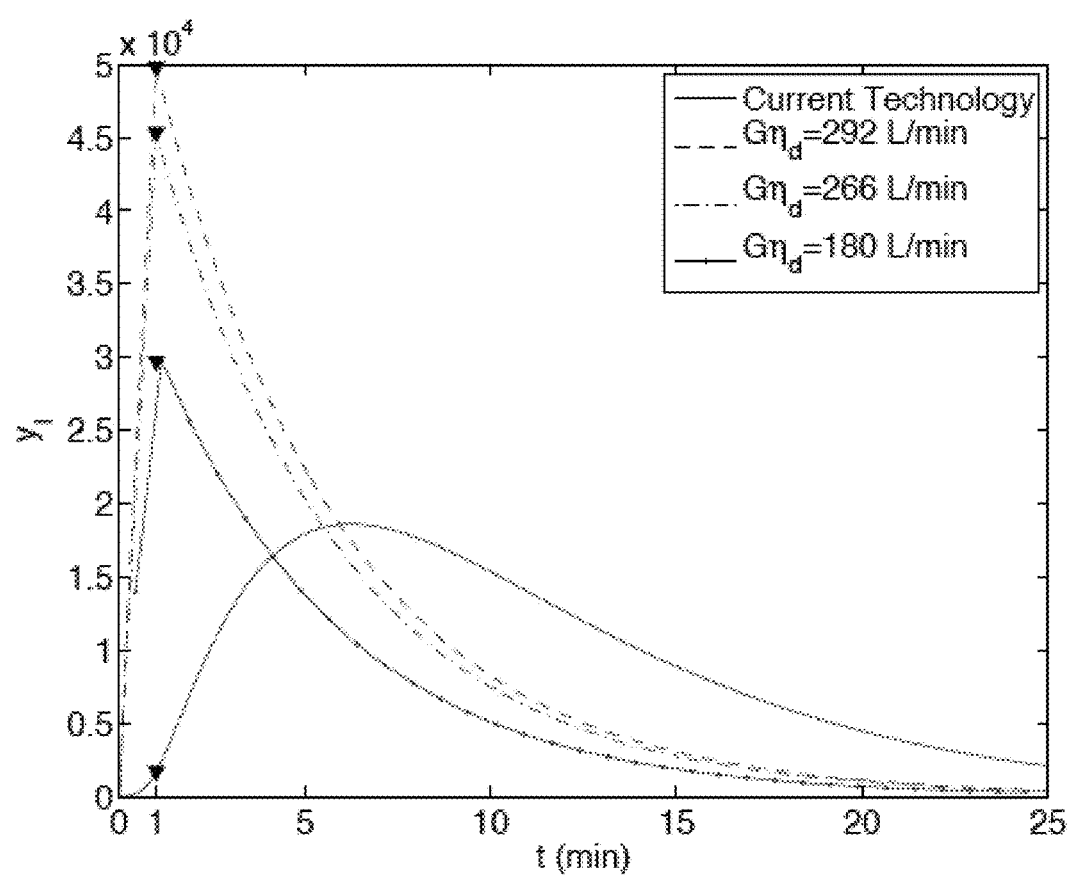

In all three scenarios, the parameters f, L and $V_1$ are fixed. The value of f was obtained from previous work while the values of L and $V_1$ were set to the existing system's specifications. The first scenario of G and $\eta_d$ corresponds to values shown in italics in Table 2. As shown in FIG. 4a, the inventive system operating at $G\eta_d$=292 has a response that achieves 95% of steady-state value more than 12 min faster than the conventional system. Moreover, both FIGS. 4a and 4b show improvement in signal. ($y_l$) at the 1-minute mark by more than 29 fold. In the second scenario, $G\eta_d$ is set at 266 to match the steady state signal of the existing system with step input. The inventive system has a faster response time (7 min 15 sec) than the existing system and amplifies the signal about 27 times in the first minute. The third scenario, with $G\eta_d$=180, presents a system with a steady state value that lags that of the conventional system. However, even with a deficient $G\eta_d$, the inventive system still outperforms the existing system at the first minute by 18 times.

As shown, the existing system produces a maximum signal at around 5 mins after the input signal consistent with experimentally reported values of 15 min for full detection cycles using currently employed systems. Accordingly, the time-savings are significant given requirements to get below 1 min detection in some applications. (See, e.g., J. Vitko, Technical. Report, The National. Academies Press, (2005), the disclosure of which is incorporated herein by reference.) What is more, the increase in the signal allows more flexibility with the limits of detection (LOD) of current sensors.

Example 2: Study of Cell Break-Up

Studies have been conducted using the experimental apparatus described in Example 1, above, to show that airborne bacteria passing through an aerodynamic shock breaks-up by experiencing a relative deceleration because of sharp changes in the gas velocity. An aerodynamic shock is created by operating the impactor nozzle at sonic velocity when $\chi=P_1/P_0<0.53$ ($P_1$ is the pressure downstream and $P_0$ is the pressure upstream of the nozzle). Uncontrolled instabilities in the form of waves on the surface of the bacterium perpendicular to the direction of acceleration cause bacterial cells to break-up. The critical acceleration ac is given by:

$$a_c = 4\pi^2 \frac{\sigma}{\rho_p d_p^2} \quad [\text{EQ. 3}]$$

where $\sigma$ is the surface tension of the bacterium, dp is the diameter of the bacterium, and $\rho p$ is the density of the bacterium. (See, e.g., D. D. Joseph, et al. *International Journal of Multiphase Flow*, 25(6-7):1263-1303, (1999); Sislian (2009) & Sislian (2010), the disclosure of each of which are incorporated herein by reference.)

The critical acceleration for two different test bacterial aerosols are shown in Table 3 below, which shows the cell properties for *E. coli* and *B. atropheus* and critical shock properties needed to induce bacterial break-up. The values are reported for 0.5 μm spores.

TABLE 3

Summary of Cell Break-up Parameters

| Cell | Gram stain | State | $a_p$ (μm) | $\sigma$ (N/m) | $A_c$ (m/s$^2$) |
|---|---|---|---|---|---|
| *E. coli* | −ve | Vegetative | 1 | $7.5 \times 10^{-3}$ | $3.0 \times 10^8$ |
| *B. atropheus* | +ve | Spore | 0.5 | $9.6 \times 10^{-2}$ | $1.6 \times 10^{10}$ |

Figure 5:
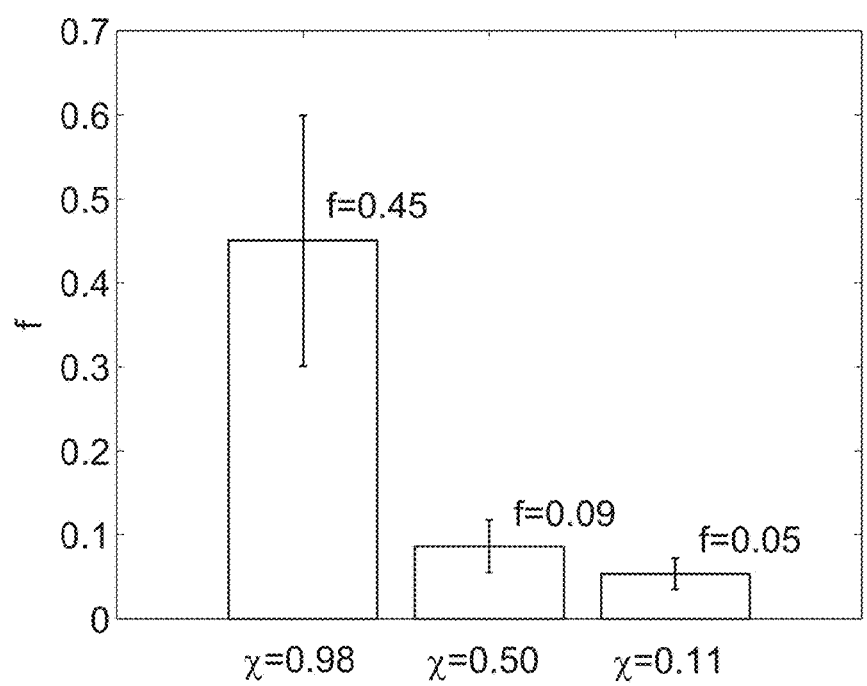
FIG. 5 provides a data graph showing the measured values of f for different operating conditions.

Previous calculations predict the break-up of both *E. coli* and *B. atropheus* spores when compared to the ac in Table 3. (See, Sislian, (2010), cited above.) Experimentally measured values of f (see Example 1, above) are shown in FIG. 5 for different operating conditions ($\chi$) of the impactor with x/d=1.2. The calculated maximum accelerations ($a_{max}$) for $\chi$=0.11, 0.50 and 0.98 are $5.0\times10^9$, $2.0\times10^8$ and $1.7\times10^6$ m/s$^2$, respectively. For $\chi$=0.11 and 0.50 the value of f is less than 0.1 consistent with the computational predictions (FIG. 5). In previous studies, the fraction of live cells (fl) was reported instead of fraction of intact cells (f). (See, Sislian, (2010), cited above.) For the current one-nozzle design, f is a function of two variables: geometry and operating conditions (f=f(x/d,$\chi$)). These studies, taken in combination, provide evidence that the impactor design of the inventive system is capable of reliably lysing the cells of different bacteria under regular operating conditions.

Example 3: Methods of Measuring DNA Collection Efficiency

The experimental setup provided in Example 1, can also be used to measure the collection efficiency ($\eta_d$) of the system. In such an experiment, the bacterial suspension would be aerosolized using a capillary nebulizer (TR-30-A1, Meinhard Glass Products) at a Nitrogen flow-rate of 0.2 mL/min. The suspension concentration and flow-rate will be controlled to produce single bacterial cells in the aerosol.

*E. coli* will be used as the test aerosol because (1) it does not require biosafety chambers and (2) is easily cultured and washed. In addition, *S. pneumoniae* is a vegetative bacterium expected to have an ac similar to *E. coli* vs. *B. atropheus* spores and hence a similar value of f. The ds-DNA (double stranded) in our samples will be stained with PicoGreen fluorescent dye (P11495, Life Technologies) using the protocols provided by the manufacturer and in other work. (See, W. Martens-Habbena and H. Sass, cited above.)

Quantitative data in the form of mass concentration of ds-DNA (as low as 25 pg/mL) can be obtained using a spectrofluorometer (Q32857, Life Technologies) at an excitation wavelength of 480 nm and emission at 520 nm. Purified *E. coli* ds-DNA solution of known concentration will be stained at different dilutions to obtain a standard curve of emission intensity vs. mass concentration. The ds-DNA will be measured for the following samples from different points in the setup (see FIG. 3: (1) bacterial suspension fed to nebulizer ($PG_1$), (2) same as (1) but sonicated to release internal ds-DNA ($PG_2$), (3) sample after the nebulization ($PG_3$), (4) sample after operation of the impactor ($PG_4$), (5) same as (4) but sonicated ($PG_5$) and (6) buffer as blank.) All samples will be filtered using 0.2 μm polycarbonate filter to trap intact cells and the filtrate will be stained. The value of $\eta_d$ can then be calculated as follows for the three different operating conditions $\chi$=0.98, 0.50 and 0.11:

$$\eta_d = \frac{PG_4}{PG_2(1-f)} \quad [\text{EQ. 4}]$$

where the numerator is the total extracted ds-DNA and the denominator is the total number of ds-DNA before the shock; $\varphi$ is the fraction of particles lost in the system before the impactor and is equal to 0.088 Å} 0.029; $\varphi$ is a property of the experimental setup and not that of the impactor; f is described in Example 1.

In this experiment, $PG_3$ is measured as a control to assess the effect of nebulization; PG1 is measured to determine the extracellular ds-DNA (=$PG_2$−$PG_1$) in the starting suspension. The bacterial suspension will be washed to reduce the amount of extracellular ds-DNA (<1% of PG2) to reduce errors in the calculation of $\eta_d$, which is the collection efficiency of ds-DNA from broken-up cells only. $PG_5$ is measured to ensure that the extracellular ds-DNA is higher than the starting extracellular ds-DNA.

The collection efficiency of bacterial particles ($\eta$) has been previously calculated computationally. (See, Sislian, (2010), cited above.) The steady-state Navier Stokes equations with a standard k—turbulence model are used to solve the gas dynamics. The particle dynamic equations are one-way coupled to the gas dynamic equations at low aerosol concentrations. Stochastic particle tracking is used to account for the turbulence in the impactor. Although η does not factor into EQ. 2, it is a function of geometry and operating condition of the impactor like $\eta_d$. The difference is in the particle sizes: bacteria are 1 μm while DNA particles are 10 nm.

Low-pressure impactors (Hering design) have been used previously to collect nanoparticles. (See, S. V. Hering, et al., *Environmental Science and Technology*, 12(6):667-673, (1978) & S. V. Hering, et al., *Environmental Science and Technology*, 13(2):184-188, (1979), the disclosures of each of which are incorporated herein by reference.) The particle collection efficiencies for 10 nm particles have been shown to increase with increasing x/d and decreasing χ, consistent with the trends in amax. (See, O. Abouali and G. Ahmadi, *Journal of Nanoparticle Research*, 7(1):75-88, (2005), the disclosure of which is incorporated herein by reference.)

The collection efficiency ($\eta_d$) can be calculated using the developed FLUENT code. In this simulation 10,000 DNA particles will be released right after the shock instead of the inlet impactor and counted as they enter the opening of the collection tube (FIG. 3). Preliminary simulation results on bacterial collection efficiency (η) indicate the entrance diameter (de) of the collection tube can be expanded to increase η without affecting $a_{max}$. When the diameter is changed from 0.5 mm to 1 mm the collection efficiency of 1 μm particles goes from η=0.37 to η=1 while the $a_{max}$ goes from $5.0 \times 10^9$ to $4.4 \times 10^9$ m/s², respectively. The change in geometry does not effect the deceleration of bacterial particles through the shock; hence will not effect the value of f ($\neq f(d_e)$). Therefore, multiple $\eta_d = \eta_d(x/d, d_e, \chi)$ can be simulated to obtain a one-nozzle geometry that enables the design of an impactor with an optimal. $G\eta_d$=266 L/min.

In order to reach $G\eta_d$=266 L/min, the threshold for a viable impactor, both G and $\eta_d$ have to be sufficiently large. In fact, G has to be greater than $G\eta_d$=266 L/min since $\eta_d$<1. In one embodiment, G may be improved by operating multiple one-nozzle geometries such as those described in Example 1, above, in parallel. In order for the nozzles to be parallel, the gas flow structures should not interact, thereby having each nozzle act as if it had no neighbors. This ensures that $\eta_d$ and f stay constant. For example, with a nozzle diameter d=1 mm (9.4 L/min per nozzle), 36 nozzles are needed to reach a G=325 mL/min. If the computed separation were 3 mm (to be determined by simulation of two nozzles) arranged in a square, a 2.1 cm×2.1 cm area is needed. This does not change the overall dimensions of the impactor. The only change will be in the pumping power requirements, which can be easily estimated by multiplying the downstream pressure by the flow-rate.

Example 4: Theoretical TB Study

The following discussion will use tuberculosis (TB) as an example to describe the advantages of the aerosol biological collector/analyzer system of the instant invention. However, it should be understood that the basic concepts described are equally applicable to other bacterial diseases. TB is among the leading causes of disease and death worldwide, which, in 2008 caused an estimated 1.3 million deaths. According to the World Health Organization (WHO), one third of the world's population is currently infected with TB and someone is newly infected every second. In developing countries, Sputum Smear Microscopy (SSM) is the most common diagnostic approach. SSM typically has a specificity of 0.97, a sensitivity of 0.51, and a response time of 2-7 days (See, e.g., Keeler, E., et al., *Nature Reviews: Diagnostics*, 61006:49-57, (2006), the disclosure of which is incorporated herein by reference.) The slow response time results in a loss of patient follow-up. Because the collection of sputum is a multistep process, some adult samples are diluted with saliva and contain insignificant amounts of *M. tuberculosis* bacterium. Therefore, a method that can provide better specificity, sensitivity, response time and sample collection will greatly enhance the diagnosis of a curable disease.

In addition, obtaining sputum from children, who account for some 11% of the TB positive population, is difficult and demands special procedures such as expectoration, gastric aspirates, and sputum induction; all of which are unpleasant for both health care providers and the children. Moreover, the quality of these samples, whenever obtainable, is also lower than that obtained from adults. By eliminating the multistep process of sputum collection, the airborne bacterial detection system of the instant invention also reduces variability in the quality of samples collected from adult patients. Furthermore, patients in underdeveloped areas often do not have the means to return to a clinic for follow-up (10-15% of all patients). By combining the collection of the sample and the detection of the *M. tuberculosis* DNA, the device of the instant invention will be able to obtain TB readings on the order of minutes to hours, which eliminates the loss of follow-up, resulting in an estimated 95,000 Annual. Adjusted Lives Saved (AALS). (See, again, Keeler, (2006), cited above.) In addition, the biosensor will also provide better sensitivity and specificity compared to the standard SSM technique. The total potential of AALS using the new device is 625,000, a significant improvement over current methods.

Again, using TB as an example, a typical. TB patient produces approximately 3000 and 40,000 infectious droplets containing *M. tuberculosis* with each cough or sneeze, respectively. As depicted in FIGS. 1a1 and 1a2, these droplets (16) serve as the starting sample for the diagnosis of TB patients using the aerosol biological collector/analyzer system of the instant invention. According to these statistics, an average of four coughs would produce enough cells collected in 1 ml to exceed the current detection limit of SSM (>10,000 cells/ml). One way to determine the efficacy of the current system for a test case like TB would involve performing an experiment on the apparatus described in Example 1 with 4 nebulizations (to simulate 4 coughs) resulting in approximately 12,000 droplets. In such an experiment, the mass concentration of ds-DNA (y) will be measured and recorded for each run. For each concentration of bacterium ($x_i$, 1<i<c) in the suspension that is fed to the nebulizer, multiple runs (N) will be conducted. The concentrations (xi) could be varied to mimic patients with TB and without TB. A threshold value for the ds-DNA concentration would be chosen based on the derived specificity and sensitivity of the entire experimental data set to determine the proportion (N') of the total runs (N) that give a reading that matches the input concentration (for $x_i$=0 cells/ml the reading that matches is a mass concentration of ds-DNA (y) below the threshold). In one embodiment, a non-discriminating dye, which is sufficient to establish the efficacy of TB sample collection could be used. In a more advanced case, a specific biosensor may be used to discern between different bacteria. In addition, the collection and biosensor modules may be integrated, and a mask for human testing used to replace the nebulizer.

SUMMARY

In summary, an aerosol biological collector/analyzer system has been described that shows dramatically improved performance over conventional systems in every measurable facet. It is well-accepted that the performance of such biosensor systems is assessed by: (1) time and efficiency to extract and deliver ICs to the sensor, (2) interference with post-lysis steps, (3) cost and (4) ability to directly interface with a patient. The first point is addressed in the discussion provided above in Examples 1 to 3. In particular, the inventive device collects directly into the impactor without another chamber being present between the patient and the impactor. This allows adequate concentrations of bacteria to be collected.

- The inventive device does not fractionate the air particles by size. This allows particles to be collected in one stage instead of fractionating the same sample on different stages, allowing for more concentrated samples with the same amount of outflow by the patient.
- The inventive device collects bacteria and bacterial components directly in a liquid sample. This allows for easy extraction of the sample and avoids contamination by the exposure of the sample. This also allows for both batch and inline sampling.
- The inventive device can collect both intact bacteria and broken-up bacteria (via shock operation).
- Compared to conventional two-chamber systems, the inventive system is compact and simple.
- Finally, conventional systems typically require the use of chemical methods, which require storage of reagents and in some cases specialized microfluidics. While miniaturization using microfluidics reduces dead volumes (τ) adds cost. In addition, some microfluidic systems produce local heating, which can denature proteins. Further, they need to be operated in a batch mode, which can take anywhere from 30 s-4 mins.

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. An aerosol biological collector/analyzer system comprising:
   a patient interface having first and second ends and defining a fluid path there between, wherein the first end is capable of engaging the patient such that at least a portion of the outflow of breath from the patient including any biological particulates contained therein is captured by the interface as a gaseous sample;
   an interconnecting tube having first and second ends and defining a fluid path there between, wherein the first end of the interconnecting tube engages and interlocks with the second end of the patient interface;
   an aerodynamic impactor having first and second ends and defining a fluid path there between, wherein the first end of the impactor engages and interlocks with the second end of the interconnecting tube, and wherein the aerodynamic impactor applies an inertial deceleration force to the gaseous sample, and wherein the magnitude of the inertial force can be varied such that at a low inertial force any biological particulates within the sample are passed through the impactor intact and that at an inertial force above a threshold any biological particulates within the sample are lysed to release the internal components thereof;
   a collection vessel having first and second ends and defining a fluid containing body, wherein the first end of the collection vessel engages and interlocks with the second end of the impactor, wherein a liquid medium for preserving the one of either the intact bacterial particulates or the internal components of the biological particulates from the gaseous sample is disposed within fluid containing body, and
   wherein an outlet is formed in fluid communication with the fluid containing body to allow for the collection of the material within the fluid containing body;
   wherein the impactor is comprised of a converging nozzle defining the fluid path of the impactor, and a flat collection surface disposed distal to said converging nozzle and perpendicular to the flow path, the flat collection surface having an inlet orifice disposed therein and aligned with the fluid path of the converging nozzle, and wherein the inlet orifice is in fluid communication with the second end of the impactor;
   a pump in fluid communication with the system for creating a flow pressure from the first end of the interface to the collection vessel such that the gaseous sample is urged through the fluid path defined by the interconnecting tube and impactor into the collection vessel;
   wherein the interconnecting tube further comprises at least one flow compensating auxiliary inlet disposed traverse to an axis of the interconnecting tube, having a first end fluidly interconnected with the interconnecting tube, and a second end that provides an outlet to the atmosphere; and
   wherein the pump and the at least one flow-compensating auxiliary inlet are configured to operate in conjunction to impose a steady-state flow condition on the gaseous sample from the interface through the impactor to the collection vessel such that the gaseous sample flows through the impactor and into the collection vessel at a steady-state rate.

2. The system of claim 1, wherein the interface comprises a fullface constant positive airway pressure mask that collects the full outbreath of the patient.

3. The system of claim 1, wherein the at least one auxiliary compensating inlet is disposed at an angle to the interconnecting tube of greater than 90 degrees.

4. The system of claim 1, further comprising a filter disposed at the second end outlet of the auxiliary compensating inlet.

5. The system of claim 4, wherein the filter is a high efficiency particulate air (HEPA) filter.

6. The system of claim 1, wherein the sample pressure downstream ($P_1$) of the nozzle and the sample pressure upstream ($P_0$) of the nozzle follows the inequality $P_1/P_0<0.53$.

7. The system of claim 1, wherein the distance from the nozzle to the collection surface (x) and the diameter of the nozzle (d) have the following ratio $x/d=1.2$.

8. The system of claim 1, wherein the sample-facing surface of the nozzle is mirror polished.

9. The system of claim 1, wherein the impactor comprises more than one nozzle.

10. The system of claim 1, wherein the second end of the collection vessel tapers toward the outlet formed in fluid communication with the fluid containing body.

11. The system of claim 1, wherein the distance between the first end of the collection vessel and the surface of the liquid medium is approximately 4 mm.

12. The system of claim 1, wherein the outlet formed in fluid communication with the fluid containing body allows sampling of the material within the fluid containing body without opening any other portion of the system.

13. The system of claim 12, wherein the outlet formed in fluid communication with the fluid containing body is configured to form a fluid connection with a syringe.

14. The system of claim 1, wherein the liquid medium is a buffer.

15. The system of claim 1, further comprising a sensor capable of detecting bacterial particulates from the sample, the sensor being disposed in fluid connection with the collection vessel.

16. The system of claim 1, wherein the interconnections between the components of the system comprise quick-disconnect couplings having valves such that once disconnected the valves automatically close.

17. The system of claim 1, wherein the components of the system are sterilizable.

18. The system of claim 1, wherein sample facing surfaces of the system are formed from a plastic material.

19. A method of collecting and analyzing an aerosol sample for bacterial infection comprising:

collecting an oscillating outflow of breath from a patient including any biological particulates contained therein as a gaseous sample using a patient interface;

transporting the sample to an impactor via an interconnecting tube;

selecting the magnitude of an inertial force to be applied to the sample, wherein the magnitude may be varied such that any bacterial particulates within the sample are passed through the impactor intact or such that any bacterial particulates within the sample are lysed to release the internal components thereof;

applying the selected inertial force to the sample using the impactor;

collecting the one of either the intact biological particulates or the internal components of the biological particulates in a fluid medium as an analyte solution for analysis in a collection vessel; and further comprising imposing a steady-state flow condition on the oscillating outflow from the patient during the collecting, transporting, applying and collecting steps such that the gaseous sample flows through the impactor and into the fluid medium at a steady-state rate.

20. The method of claim 19, further comprising analyzing the analyte solution for bacterial contaminants in real-time.

21. The method of claim 19, further comprising withdrawing a batch sample of the analyte solution for analysis.

* * * * *